US005428026A

United States Patent [19]
Colarow

[11] Patent Number: 5,428,026
[45] Date of Patent: Jun. 27, 1995

[54] LIPOSOLUBLE ANTIOXIDANT MIXTURE

[75] Inventor: Ladislas Colarow, Savigny, Switzerland

[73] Assignee: Nestec S.A., Vevey, Switzerland

[21] Appl. No.: 872,090

[22] Filed: Apr. 22, 1992

[30] Foreign Application Priority Data

May 24, 1991 [EP] European Pat. Off. ............ 91108412

[51] Int. Cl.$^6$ .................. A61K 31/355; A61K 31/44; A61K 31/685
[52] U.S. Cl. ..................................... 514/78; 514/350; 514/355; 514/458; 514/904
[58] Field of Search ................ 514/904, 80, 78, 251, 514/264, 276, 355, 350, 458; 260/398.5

[56] References Cited

U.S. PATENT DOCUMENTS

| 2,432,698 | 12/1947 | Taub et al. | 260/398.5 |
|---|---|---|---|
| 2,433,688 | 12/1947 | Fox et al. | 514/904 |
| 2,662,048 | 12/1953 | Winsten | 514/904 |
| 3,036,957 | 5/1962 | Lehman | 514/904 |
| 3,332,848 | 7/1967 | Magid | 514/904 |
| 4,537,782 | 8/1985 | Millet et al. | 514/774 |
| 4,567,161 | 1/1986 | Posanski et al. | 514/23 |
| 4,765,927 | 8/1988 | Nomura et al. | 252/400.2 |
| 5,114,716 | 5/1992 | N'Guyen et al. | 424/401 |

FOREIGN PATENT DOCUMENTS

| 158090 | 2/1985 | European Pat. Off. | 424/59 |
|---|---|---|---|
| 0326829 | 8/1989 | European Pat. Off. | A61C 7/00 |
| 238059 | 6/1946 | Switzerland | 514/276 |
| 902377 | 8/1962 | United Kingdom | A61C 7/00 |

OTHER PUBLICATIONS

Cillard et al., "Revue Francaise des Corps Gras", 34, Nos. 5-6, pp. 271-274 (1987).
Cillard, et al. "Antioxidant activity of associated alpha-tocopherol and ascorbic acid in aqueous media," 2398 Revue Francaise des Corp Gras, 34(1987) May, Jun., Nos. 506, pp. 271-274.

Primary Examiner—Alan L. Rotman
Attorney, Agent, or Firm—Vogt & O'Donnell

[57] ABSTRACT

A liposoluble antioxidant composition contains a group B vitamin-organic acid complex and a lecithin rich in phosphatidyl choline.

8 Claims, No Drawings

LIPOSOLUBLE ANTIOXIDANT MIXTURE

BACKGROUND OF THE INVENTION

This invention relates to a liposoluble antioxidant mixture based on an organic acid.

The advantage of presenting antioxidant organic acids in a liposoluble form is due to the fact that they have an inhibiting effect on the oxidation of lipids in biological systems. In combination with vitamin E, vitamin C, for example, has a synergistic antioxidant effect because, as a reducing agent, L-ascorbic acid converts the tocopheroxyl derivatives into tocopherols which are capable of refixing the free radicals in the form of tocopheroxyl derivatives.

Hydrophilic L-ascorbic acid can be made liposoluble by esterification of its hydroxyl groups in the 5 or 6 position with a fatty acid. Thus, 6-O-palmitoyl-L-ascorbic acid or ascorbyl palmitate is used as an additive for protecting fats against oxidation and also as a source of vitamin C. However, this compound has the disadvantage of dissolving very slowly in fats at temperatures at which they are not degraded. Accordingly, it has been necessary to add partial glycerides or complex lipids, for example soya lecithin. Even with these additives, however, the incorporation of ascorbyl palmitate at a level guaranteeing an adequate antioxidant effect can only be carried out at a relatively high temperature of the order of 130° C. for a certain time, for example 30 minutes, which induces degradation of the fats and the antioxidant itself, which has a melting point of 115.5° C.

European patent application European Patent Application O 0 326 829, for example, relates to the production of a liposoluble antioxidant mixture containing ascorbic acid which is solid at room temperature, and which is based on polar lipids, such as lecithins. A mixture such as this may readily be used in dry solid products. However, its incorporation in oils rich in heat-sensitive polyunsaturated fatty acids requires the use of a polar solvent, for example ethanol, which has to be subsequently eliminated. In addition, its incorporation in products containing water, for example emulsions, is problematical because, in the presence of water, ascorbic acid has a tendency to cause degumming of lecithin which has an adverse effect on their stability.

In addition, according to U.S. Pat. No. 2,432,698 for example, vitamins A and B can be protected against oxidation by addition of niacinamide. In cases where these vitamins have to be stabilized with an oil as support, optionally in the presence of tocopherol, it is necessary according to this patent to add natural solvents, such as ethyl and lauric alcohols, for example, to the mixture as niacinamide is not liposoluble.

SUMMARY OF THE INVENTION

The object of the present invention was to solve the problem of incorporating organic acids, particularly ascorbic acid, in a liposoluble antioxidant mixture consisting of natural ingredients which would not have the disadvantages mentioned above and which could be incorporated both in anhydrous products and in water-containing products, for example in emulsions.

The antioxidant mixture according to the invention is characterized in that it comprises or may consists of a complex of group B vitamin and organic acid and a lecithin containing at least 40% by weight phosphatidyl choline.

Among the vitamins of group B, pyridine bases, for example niacinamide, pyridoxine or pyridoxamine, are preferred, niacinamide being particularly preferred.

In the context of the invention, an organic acid is understood to be a polyacid capable of forming a complex with a group B vitamin base, such as for example citric acid, tartaric acid, or preferably, ascorbic acid.

In the context of the invention, the lecithin used is preferably a soya lecithin fraction soluble in ethyl alcohol. This fraction is zwitterionic, i.e., stable over a wide pH range, and contains few complexable phospholipids. The lecithin is preferably present in the form of a mixture containing approximately 40 to 50% by weight phosphatidyl choline and approximately 50 to 60% by weight vegetable oil, for example soybean oil, a medium-chain triglyceride ($C_{8-10}$ fatty acid triglyceride) or cocoa butter.

DETAILED DESCRIPTION OF THE INVENTION

To prepare the liposoluble antioxidant mixture of the present invention, the complex of organic acid and group B vitamin, for example niacinamide ascorbate, is preferably dissolved in a solvent of food quality, for example ethanol, which has preferably been degassed. The complex itself may be prepared, for example, by moderate heating of an equimolar mixture of niacinamide and ascorbic acid in a suitable polar solvent, for example ethyl alcohol, acetone or water. The complex may be dissolved by moderate stirring at a temperature of 40° to 50° C., preferably in an inert atmosphere, for example of nitrogen, in a concentration of 2 to 10 g complex to 100 ml solvent. If necessary, d,l-alpha-tocopherol is then added.

Alternatively, the group B vitamin, the organic acid and the vitamin E may be directly dissolved in the solvent under the same conditions as before, providing the group B vitamin and the organic acid are used in equimolar proportions so that the complex can be formed. 5 to 10 parts by volume of this solution are then mixed with 1 to 2 parts by volume lecithin which dissolves rapidly with moderate stirring at 50° to 60° C., preferably in an inert atmosphere. The solution may then be concentrated by removing the solvent, for example by distillation in an inert gas atmosphere at 60° to 65° C., after which any trace of residual solvent may be eliminated, for example by bubbling through an inert gas at ambient temperature. The mixture obtained is in the form of a translucent solution light yellow in colour similar to a refined vegetable oil and having the viscosity of a standard commercial soya lecithin, i.e., containing approximately 30 to 40% soybean oil. It is amber in colour, translucent, odourless and stable to heat.

The antioxidant mixture may be stored in the absence of light at ambient temperature.

It may be used as such and may readily be incorporated in an oil intended to be protected against oxidation, for example in an oil rich in unsaturated fatty acids, preferably in a quantity of from 1 to 25% by weight.

In one preferred embodiment, the antioxidant mixture may be presented in a more fluid form and may contain, for example, a medium-chain triglyceride.

In one particularly advantageous embodiment from the point of view of antioxidant activity, the mixture additionally contains tocopherol to produce a synergistic effect. The tocopherol used may be alpha-tocopherol, beta-tocopherol, gamma-tocopherol, delta-tocopherol or a mixture of these tocopherols, for example a natural mixture emanating from the unsaponifiable fraction of a vegetable oil, for example soybean oil, wheat germ oil, cottonseed oil. The tocopherol may be added to the antioxidant mixture or may be naturally present in the oil intended to be protected.

The antioxidant mixture advantageously contains 1 to 5% and preferably about 2.5% by weight tocopherol and 2.5 to 30% and preferably 5 to 20% by weight complex, for example niacinamide ascorbate.

The antioxidant mixture may serve as a support for other liposoluble vitamins, for example vitamin A, and may form a micronutriment of high nutritional value when it contains MCT for example.

Similarly, it may serve as a vitamin support intended for incorporation in the lipid phase during the preparation of a dietetic food, such as for example aninfantmilk, and thus forms a particularly advantageous means of introducing vitamins B and C which are not liposoluble.

The antioxidant mixture may be incorporated in a food product containing an unsaturated fat, particularly a vegetable oil, for example wheat germ oil, black currant seed oil, Kiwi oil, corn oil, soybean oil, safflower oil, olive oil, evening primrose oil, borage oil, or an animal fat, such as butter oil, chicken fat and, more particularly, a fish oil.

This food product may be, for example, a salad dressing or a dietetic product.

By virtue of its low acidity (pH≧4), the antioxidant mixture according to the invention may readily be encapsulated, for example in gelatine capsules, without the residual water associated with the gelatine leading to degumming of the lecithin in the event of prolonged storage.

The antioxidant mixture may be used to protect lipids against oxidation in compositions intended for enteral and parenteral consumption. The antioxidant mixture may also be used to protect lipids in cosmetic compositions against oxidation.

EXAMPLES

The invention is illustrated by the following Examples in which parts and percentages are by weight, unless otherwise indicated.

EXAMPLE 1

96.7 g niacinamide ascorbate are dissolved in 5 l ethanol (degassed beforehand by sonication to eliminate free oxygen) with moderate stirring at 50° C. in a stream of nitrogen, after which 28.1 g d,1-alpha-tocopherol are added to the resulting solution. This solution is then pumped into a 25 liter rotary evaporator flask filled beforehand with 1,000 g lecithin containing 45% soya phosphatidyl choline dissolved in safflower oil at 50° C., which results in rapid dissolution of the lecithin, this operation being carried out in a stream of nitrogen. A translucent solution free from insoluble constituents is thus obtained. The solution is then concentrated in a gentle stream of nitrogen at 60° C. until the solvent has completely evaporated and, after the solution has been cooled to ambient temperature, every trace of residual solvent is eliminated by bubbling nitrogen through the solution. The liposoluble antioxidant mixture obtained is pale yellow in colour and has a viscosity similar to that of a standard commercial lecithin. It has the following composition:

|  | % |
| --- | --- |
| d,1-alpha-tocopherol | 2.5 |
| Vitamin C (as niacinamide ascorbate) | 5 |
| Vitamin B3 (as niacinamide ascorbate) | 3.6 |
| Phosphatidyl chloline | 40 |
| Safflower oil | balance to 100 |

EXAMPLE 2

To prepare a liposoluble antioxidant mixture more fluid than that of Example 1, Example 1 is repeated with addition of 2,000 g of a lecithin consisting of 45% phosphatidyl choline, 50% medium-chain ($C_{8-10}$) triglyceride and 5% other phosphatides.

EXAMPLE 3

A liposoluble antioxidant mixture is prepared in the same way as in Example 1 except that the lecithin used contains 45% phosphatidyl choline, 50% cocoa butter and 5% other phosphatides.

EXAMPLE 4

A liposoluble antioxidant mixture is prepared in the same way as in Example 1 except that the lecithin used contains 45% phosphatidyl choline, 50% soybean oil and 5% other phosphatides.

EXAMPLE 5

A liposoluble antioxidant mixture is prepared in the same way as in Example 1 except that the lecithin used contains 45% phosphatidyl choline, 50% medium-chain ($C_{8-10}$) triglyceride and 5% other phosphatides.

EXAMPLE 6

A liposoluble antioxidant mixture is prepared in the same way as in Example 1 except that no d,1-alpha-tocopherol is added.

EXAMPLE 7

190 g niacinamide, 270 g ascorbic acid, 130 g d,1-alpha-tocopherol and 9.41 kg lecithin (containing 45–50% phosphatidyl choline for 50–55% medium-chain triglycerides) are dissolved in 8 l food-quality ethanol (94%) with gentle stirring under nitrogen at 50° C. in a 50 liter glass evaporator until a clear solution is obtained. The solution is then concentrated to dryness in a vacuum of 250–60 mb and at a temperature of 60° to 70° C. The product obtained is fluid at 50° C. and dissolves rapidly in oils and fats at 40° to 60° C.

EXAMPLE 8

4.49 g pyridoxine, 4.67 g ascorbic acid and 2.37 g d,1-alpha-tocopherol are dissolved in ethanol (94%) at 50° C., 188.47 g lecithin (containing 45–50% phosphatidyl choline for 50–55% medium-chain triglycerides) are added to the solution and the solution is then concentrated to dryness as in Example 7. The product obtained is fluid and dissolves rapidly in oils and fats at 40° to 60° C.

EXAMPLE 9

In the same way as in Example 7, 2.74 g citric acid monohydrate, 4,77 g niacinamide, 2.5 g d,1-alpha-tocopherol and 190 g lecithin (containing 45–50% phosphatidyl choline and 50–55% medium-chain triglycerides) are dissolved in 250 ml ethanol (94%), after which the solution is concentrated to dryness. The product obtained is fluid and dissolves rapidly in oils and fats at 40° to 60° C.

EXAMPLE 10

In the same way as in Example 7, 7.07 g pyridoxine, 2.93 g citric acid monohydrate, 2.67 g d,1-alpha-tocopherol and 183.33 g lecithin (containing 45–50% phosphatidyl choline and 50–55% medium-chain triglycerides) are dissolved in 250 ml ethanol (94%), after which the solution is concentrated to dryness. The product obtained is fluid at 50° C. and dissolves rapidly in oils at that temperature.

EXAMPLES 11–13

The special oils shown below are prepared simply by dissolving the antioxidant mixture of Example 1 without the d,1-alpha-tocopherol in an oil with gentle stirring under nitrogen at 40° to 50° C. and adding d,1-alpha-tocopherol to the resulting solution in the quantities indicated in Table 1 below:

TABLE 1

| Composition (g) | Example 11 | Example 12 | Example 13 |
|---|---|---|---|
| Kiwi oil rich in highly unsaturated fatty acids | — | — | 1000 |
| Black currant seed oil | 1000 | — | — |
| Fish oil rich in eicosapentaenoic acid | — | 1000 | — |
| d,1-alpha-tocopherol | 0.25 | 0.25 | 0.236 |
| Antioxidant mixture providing | 10.6 | 15.9 | 10 |
| g niacinamide ascorbate | 0.5 | 0.75 | 0.472 |

EXAMPLE 14

Gelatine capsules containing 500 mg of the mixture of Example 1 and the micronutriments indicated in the proportions indicated are prepared. The vitamin-containing nutritive preparation has the following composition:

| Composition | mg |
|---|---|
| Black currant seed oil | 280 |
| Vitamin A acetate (Dissolved in black currant seed oil) | 0.12 |
| Vitamin E as d,1-alpha-tocopherol (provided by the antioxidant mixture of Example 1) | 1.33 |
| Vitamin B2 tetrabutyrate (dissolved in black currant seed oil) | 0.3 |
| Vitamin C (as niacinamide ascorbate and lecithin provided by the antioxidant mixture of Example 1 | 2.661 |
| Vitamin B3 (as niacinamide ascorbate and lecithin provided by the antioxidant mixture of Example 1) | 1.849 |
| Soya phosphatidyl choline (as phosphatidyl choline in safflower oil) | 125 |
| Safflower oil | 125 |

The gelatine capsules are stable to prolonged storage at ambient temperature.

EXAMPLE 15

An oil intended for dressing a salad of fresh vegetables without vinegar is prepared with the following composition:

| Composition | g |
|---|---|
| Refined safflower oil containing 500 mg d,1-alpha-tocopherol | 900 |
| Antioxidant mixture of Example 1 providing 5 g vitamin C 3.6 g vitamin B3 and 40 g phosphatidyl choline | 100 |

A neutral-tasting plate of fresh vegetables may be dressed with 10 g of the above mixture so that it provides 50 mg vitamin C, 36 mg vitamin B3 and 400 mg phosphatidyl choline.

EXAMPLE 16

The induction times of black currant seed oil or kiwi oil stabilized with the antioxidant additives are determined by the RANCIMAT® accelerated oxidation test. In this test, air is passed through a test tube containing a 5 g sample of fats at 80° C. and 90° C. and the conductivity of the volatile secondary products formed during oxidation and entrained by the air stream is measured. The induction time is determined graphically from the conductivity curve recorded as a function of time by intersection of the tangent to the curve with the time axis.

The results are set out in Tables II and III below.

TABLE II

| Oil | Antioxidant additive | Induction time (h) at 80° C. |
|---|---|---|
| Black currant seed oil | — | 20 |
| Black currant seed oil | Ascorbyl palmitate (200 parts per million) | 40 |
| Black currant seed oil | Antioxidant mixture of Example 1 (1%) | 68.3 |
| Black currant seed oil | Antioxidant mixture of Example 1 (2%) | 78.3 |
| Kiwi oil | — | 5.75 |
| Kiwi oil | Hydroxybutyl anisole (600 parts per million) | 16.75 |
| Kiwi oil | Antioxidant mixture of Example 3 (1%) | 28.5 |
| Kiwi oil | Antioxidant mixture of Example 4 (1%) | 35.1 |
| Kiwi oil | Antioxidant mixture of Example 5 (1%) | 36.6 |

It can be seen that the antioxidant mixture according to the invention increases the induction time by a factor of 3.4 to 3.9 in relation to that measured without the additive and has an oxidant activity higher by a factor of 1.7 to 2 than ascorbyl palmitate in the case of black currant seed oil. In the case of kiwi oil, the mixture additionally containing tocopherol increases the induction time by a factor of 5 to 6 in relation to that measured without the additive and has an antioxidant activity higher by a factor of 1.7 to 2.2 than that of hydroxybutyl anisole.

TABLE III

| Oil | Antioxidant additive | Induction time (h) at 80° C. |
|---|---|---|
| Pure black currant seed oil | — | 20 |
| Pure black currant seed oil | Antioxidant mixture of Example 7 (2%) | 33 |
| Refined black currant seed oil | — | 10.1 |
| Refined black currant | Antioxidant mixture | 24.2 |

TABLE III-continued

| Oil | Antioxidant additive | Induction time (h) at 80° C. |
|---|---|---|
| seed oil | of Example 8 (1%) | |
| Refined black currant seed oil | Antioxidant mixture of Example 9 (1%) | 17.5 |
| Refined black currant seed oil | Antioxidant mixture of Example 10 (1%) | 18.4 |

EXAMPLES 17-20

These Examples illustrate the preparation of cosmetic skin-care compositions containing lipids of which the lipid component is protected against oxidation by addition of the liposoluble antioxidant mixture according to the invention to the lipid phase.

The nomenclature used in these Examples is the nomenclature of the "Cosmetic, Toiletry and Fragrance Association, Inc., Washington D.C." (eFTA).

To prepare the emulsions, the components of the lipid phase A are mixed and heated to 75° C. The aqueous phase B is prepared and is also heated to 75° C. and is then added to the lipid phase A with slow stirring. The mixture is then cooled to ambient temperature, i.e., approx. 25° C., with slow stirring. If desired, the constituents C are then added at that temperature in the order of the formula.

To prepare the anhydrous product of Example 20, all the constituents are cold-mixed with slow stirring in the order of the formula.

| | % |
|---|---|
| 17. Moisturizing cream (oil-in-water emulsion) | |
| Lipid phase A | |
| Peg-6-stearate, glycerol stearate and peg-20-cetyl ether (peg: polyethylene glycol) | 15 |
| vaseline oil | 5 |
| Wheat germ oil containing 1% of the antioxidant mixture of Example 6 | 3 |
| Sweet almond oil | 2 |
| Cetyl alcohol | 1 |
| Isostearyl isostearate | 2 |
| 2-Octyl dodecyl myristate | 1 |
| Lanolin wax | 1 |
| Aqueous phase B | |
| Methyl isothiazoline | 0.1 |
| Demineralized water | 59.6 |
| Protein from human placenta | 2 |
| Additives C | |
| Propylene glycol and calendula extract | 2 |
| Collagen (2) soluble in demineralized water (4) | 6 |
| Perfume | 0.3 |
| 18. Anti-wrinkle cream (oil-in-water emulsion) | |
| Lipid phase A | |
| Nonionic hydrophilic beeswax | 10 |
| Vaseline oil | 4 |
| Isostearyl isostearate | 5 |
| Ethyl linoleate | 1 |
| Mineral oil, apricot kernel oil and calendula extract | 4 |
| Sweet almond oil containing 2% of the antioxidant mixture of Example 6 | 3 |
| Apricot kernel oil | 3 |
| Aqueous phase B | |
| Methyl isothiazole | 0.1 |
| Demineralized water | 64.7 |
| Carbopol 932 (polycrosslinked acrylic acid polymer) | 0.3 |
| Triethanolamine | 0.6 |
| Propylene glycol and elder extract | 2 |
| Water-soluble collagen | 2 |
| Perfume | 0.3 |
| 19. Baby cream (oil-in-water emulsion) | |
| Lipid phase A | |
| Polyethylene glycol-6-32-stearate | 10 |
| Sweet almond oil containing 1% of the antioxidant mixture of Example 6 | 6 |
| Vaseline oil | 4 |
| Cabbage palm oil, palm oil and peg 6 | 3 |
| Stearic acid | 1 |
| Aqueous phase B | |
| Demineralized water | 67.5 |
| Glycerine | 3 |
| Methyl isothiazoline | 1 |
| Propylene glycol and calendula extract | 4 |
| Perfume | 0.5 |
| 20. Satin oil (anhydrous) | |
| Sunflower oil containing 1% of the antioxidant mixture of Example 6 | 3 |
| Caprylic and capric acid triglycerides | 30 |
| Cyclic dimethyl polysiloxane | 25.7 |
| Propylene glycol dipelargonate | 37.8 |
| Octyl methoxycinnamate | 3 |
| Perfume | 0.5 |

I claim:

1. A liposoluble antioxidant composition consisting essentially of a group B vitamin-organic acid complex, a lecithin containing at least 40% by weight phosphatidyl choline, and optionally, tocopheral.

2. A composition according to claim 1 wherein the complex is niacinamide ascotbate.

3. A composition according to claim 1 wherein the complex is pyridoxine ascorbate.

4. A composition according to claim 1 or 2 or 3 which contains tocopherol.

5. A composition according to claim 1 or 2 or 3 wherein the lecithin includes a fat selected from the group of fats consisting of a vegetable oil, a medium chain triglyceride and cocoa butter.

6. A composition according to claim 4 wherein the lecithin comprises a fat selected from the group of fats consisting of a vegetable oil, a medium chain triglyceride and a cocoa butter.

7. A composition according to claim 1 wherein the group B vitamin is a pyridine base, wherein the organic acid is selected from the group of acids consisting of citric acid, tartaric acid and ascorbic acid and wherein the lecithin is a soya lecithin fraction soluble in ethyl alcohol.

8. A composition according to claim 4 wherein the composition contains, by weight, from 2.5% to 30% complex and from 1% to 5% tocopherol.

* * * * *

UNITED STATES PATENT AND TRADEMARK OFFICE
CERTIFICATE OF CORRECTION

PATENT NO. : 5,428,026
DATED : June 27, 1995
INVENTOR(S) : Ladislas COLAROW

It is certified that error appears in the above-indentified patent and that said Letters Patent is hereby corrected as shown below:

Column 8, line 37 (line 4 of claim 1), change "tocopheral" to --tocopherol--.

Column 8, line 49 (line 2 of claim 6), change "comprises" to --includes--.

Signed and Sealed this

Nineteenth Day of September, 1995

Attest:

BRUCE LEHMAN

*Attesting Officer*  *Commissioner of Patents and Trademarks*